(12) United States Patent
Foulkes (10) Patent No.: US 7,722,669 B2
(45) Date of Patent: May 25, 2010

(54) METHOD AND INSERT FOR MODIFYING EYE COLOR

(76) Inventor: Richard Foulkes, 40 S. Clay, Hinsdale, IL (US) 60546

( * ) Notice: Subject to any disclaimer, the term of this patent is extended or adjusted under 35 U.S.C. 154(b) by 901 days.

(21) Appl. No.: 10/918,495

(22) Filed: Aug. 13, 2004

(65) Prior Publication Data

US 2006/0036318 A1 Feb. 16, 2006

(51) Int. Cl.
*A61F 2/14* (2006.01)
(52) U.S. Cl. ......................................... 623/4.1
(58) Field of Classification Search .................. 623/4.1, 623/5.11, 5.16
See application file for complete search history.

(56) References Cited

U.S. PATENT DOCUMENTS

| | | | |
|---|---|---|---|
| 4,014,335 A | 3/1977 | Arnold | |
| 4,053,953 A | 10/1977 | Flom et al. | |
| 4,452,235 A | 6/1984 | Reynolds | |
| 5,318,047 A | 6/1994 | Davenport et al. | |
| 5,322,691 A | 6/1994 | Darougar et al. | |
| 5,323,788 A | 6/1994 | Silvestrini et al. | |
| 5,336,261 A | 8/1994 | Barrett et al. | |
| 5,391,201 A | 2/1995 | Barrett et al. | |
| 5,395,618 A | 3/1995 | Darougar et al. | |
| 5,628,797 A | 5/1997 | Richer | |
| 5,722,971 A | 3/1998 | Peyman | |
| 5,733,334 A | 3/1998 | Lee | |
| 5,773,021 A | 6/1998 | Gurtler et al. | |
| 5,824,072 A | 10/1998 | Wong | |
| RE35,974 E | 12/1998 | Davenport et al. | |
| 5,843,186 A * | 12/1998 | Christ | 623/6.56 |
| 6,217,571 B1 | 4/2001 | Peyman | |
| 6,217,896 B1 | 4/2001 | Benjamin | |
| 6,280,469 B1 * | 8/2001 | Terry et al. | 623/4.1 |
| 6,306,075 B1 | 10/2001 | Shadduck | |
| 6,508,837 B1 | 1/2003 | Silvestrini | |
| 6,543,453 B1 | 4/2003 | Klima et al. | |
| 6,669,950 B2 | 12/2003 | Yaacobi | |
| 6,713,081 B2 | 3/2004 | Robinson et al. | |
| 6,855,163 B2 * | 2/2005 | Peyman | 623/5.11 |
| 7,037,337 B2 * | 5/2006 | Carriazo | 623/4.1 |
| 7,364,674 B1 * | 4/2008 | Hoover | 264/1.36 |

OTHER PUBLICATIONS

Text of Notification and Translation of Office Action for Chinese Application No. 2005800331734.5; mailing date Apr. 23, 2009; 3 pages.
Notification of the Second Office Action in China; Application No. 200580031734.5, date issued Aug. 28, 2009, 7 pages.

* cited by examiner

*Primary Examiner*—William H. Matthews
(74) *Attorney, Agent, or Firm*—Thomas, Karceski, Raring & Teague, P.C.

(57) ABSTRACT

A method and intrastroma insert are adapted to modify eye color. The insertion of opaque material into the stromal space is a means of changing the color and/or design of the stroma and, apparently, the iris. Biocompatible inserts include a slurry of biocompatible material, a fabric including opacified material, and a thin, permeable film material incorporating some opaque materials that may also alter the shape of the cornea to improve aberrational shape and may cover the pupil to block ultraviolet radiation and provide sun protection with polarizing effect.

10 Claims, 5 Drawing Sheets

METHOD AND INSERT FOR MODIFYING EYE COLOR

The present invention relates to a method for insertion of photo absorptive and/or photo reactive material within the cornea of an eye, specifically within the stroma, for modifying eye color and other aspects of appearance, normalizing iris deficiencies and structure, absorbing radiation, and correcting aberrational corneal anatomy. The insert is formed of biocompatible, noneroding and positionally stable materials, such as hydrogels and hydrogel polyacrylamides, implantable in the stroma.

BACKGROUND

The iris is an anatomic structure that defines and surrounds the pupillary aperture that allows light into the eye's interior. Pigment in the iris, specifically the amount and color of the pigment, determines human eye color. The primary function of the iris, along with the eyelids, is to control the amount of light that reaches the retina. Excessive exposure to sunlight may contribute to cataracts and age-related macular degeneration. People with insufficient pigment in the iris are prone to these diseases and to poor vision from glare and lens effects from the rim of the human lens. The greater the amount of pigment in the eye, the darker the color of the iris. Darker iris color provides greater protection from ultraviolet ("UV") light and makes eyes less sensitive to bright light. Most of the world's population has darker eye color.

In addition to the biological function, the iris is the eye's most significant cosmetic feature. Color and patterns in the iris contribute to the belief that the eyes are the "window to the soul."

Historically, radial tinted contact lens have been the primary method used to adjust the apparent color of the iris, but contact lenses have substantial and well-recognized limitations in this regard. For example, contact lenses are typically readily distinguishable from natural eye color. The lenses "float", thereby moving the tinted portion over the pupil and causing the eyes to appear to be looking in different directions. Contact lenses also present risks of infection to the cornea, which in turn can lead to scarring and poor vision. Contact lenses are inconvenient, because they generally should be removed on a daily basis to minimize the risk of infection. Even so, contact lenses are not a viable option for a significant portion of the population, including those with dry eyes or other intolerance factors.

Substantial research and clinical study exist with respect to eye implants for purposes of improving the refractive performance of an eye and thereby improving vision. These corrective implants are transparent and often involve positioning within or near the pupillary axis—the eyes direct line of sight. The implants are shaped and dimensioned to modify the angulation of light rays passing through the cornea to change the eye's refractive properties.

A new permanent or semi-permanent alternative means of coloring the eye would have several immediate benefits. Eliminating the need for contact lenses would eliminate contact lens-related infections and problems that result from mishandling, such as leaving a lens in the eye too long. Darkening the cornea of those with little or no iris color due, for example, to genetic circumstances would reduce excessive sunlight exposure to the retina, improve vision and provide a desirable cosmetic enhancement. Using corneal opacification to make light exposure relatively uniform in those with surgical or traumatic irregularities of the iris would provide similar benefits. Mitigating iris color flaws would improve self-image and potentially improve vision. Providing a widely available means of cosmetically enhancing eye color would provide a means for self-expression and potentially improve vision.

"Aberration" is distortion in the shape of the cornea leading to misdirection of the light ray off the desired path to the center of vision the macula. A common form of aberration is called spherical aberration and is the tendency of the cornea to curve away from the midline or visual axis too quickly. This leads to progressive steepening at the rim and near sightedness that is greater at the rim than the center.

Wavefront analysis is performed by an aberometer. The aberometer can detect optical errors at a fine level. Wavefront analysis assesses every ray of light that enters the eye and then determines what changes will produce the clearest image. Aberometers precisely measure the overall refractive error of the entire eye and point out common errors of refraction that are not apparent to the older methods. The peripheral part of the cornea is a cause of aberration in many eyes and this is uncovered with dilation of the pupil with these instruments. Spherical aberration and its variants are the common finding in many eyes.

SUMMARY

It is an object of the present invention to overcome the foregoing drawbacks and limitations of existing eye color modification methods, permit the modification of other aspects of the eye's appearance, provide an improved means of normalizing iris deficiencies and structure, and provide a means of absorbing radiation and correcting aberrational corneal anatomy through the use of biocompatiable, noneroding and positionally stable materials, such as hydrogels and hydrogel polyacrylamides, implanted in the stroma.

In one example, a method of modifying eye color includes forming a channel within a plane around the pupil of an eye, wherein the channel is located in the stroma portion of the eye. The cornea of the eye is slitted to gain access to the channel. A biocompatible material is then inserted into the channel, wherein the biocompatible material is at least partially opacified. The channel may be formed by using a laser technique. The channel may be formed by using a surgical blade. The channel may comprise a substantially flat, annular shape having an outer diameter proximate the limbus of the eye. The inside diameter of the annular shape may be proximate the daylight margin of the pupil. The channel may extend around the entire circumference of the pupil. The biocompatible material may be comprised of a slurry of particles with at least some of the particles comprising an opacified material. The shape of the particles may include a uniform or varied collection of two- and/or three-dimensional shapes, including, for example, flat, round, spherical, oval, polygon, diamond, star, and triangular shapes and combinations thereof.

The biocompatible material may be comprised of an opacified polymer fabric, film or mesh, or an opacified biofilm. Depending upon the application and desired outcome, the film may be opacified or clear UV absorbing material that may cover the pupil. The films would be expected to have a thickness of approximately 3 microns or less. Additional applications may include thicker inserts with pre-printed designs.

In another example, an intrastromal eye insert comprises a biocompatible material that is at least partially opacified. The biocompatible material may comprise a slurry of particles with at least some of particles comprising an opacified material. The biocompatible material may be comprised of a polymer fabric comprising an opacified material. The biocompatible material may be comprised of a thin polymer film comprising an opacified material.

DETAILED DESCRIPTION

The invention is directed to an intrastromal insert adapted to modify eye color and provide therapeutic benefits addressing the problems of insufficient or inconsistent pigment in the iris. The invention is further directed to a method of placing an insert into the stromal space to modify eye color. The invention is further directed to a method of placing an insert into the stromal space to filter UV radiation and in some cases to mute or absorb visible light entering the pupil.

The materials that may be used for insertion into the stroma include biocompatiable, noneroding and positionally stable materials, such as hydrogels and hydrogel polyacrylamides. These materials may include or encapsulate pigments, materials that reflect or absorb light or combinations of both, photosensitive materials (including photochromic and thermochromic materials), a colored or multi-colored mesh, biofilm (clear and light-filtering) that is placed in the stroma but extends over the pupil to filter UV or other radiation and to filter visible light, including through the use of photograying or otherwise photoreactive film, including for use by people with extreme photo-sensitivity. While the invention is described herein in the context of several examples, those of skill in the art will understand that additional materials may be used as an insert and different methods may be used to place that insert within the stromal space in a variety of patters and forms described or depicted below.

The methods for inserting the materials into the stromal space as described herein include, for example, the use of a femtosecond pulsion laser or other laser, a microkeratome or other bladed device, or a microneedle.

Figure 1:
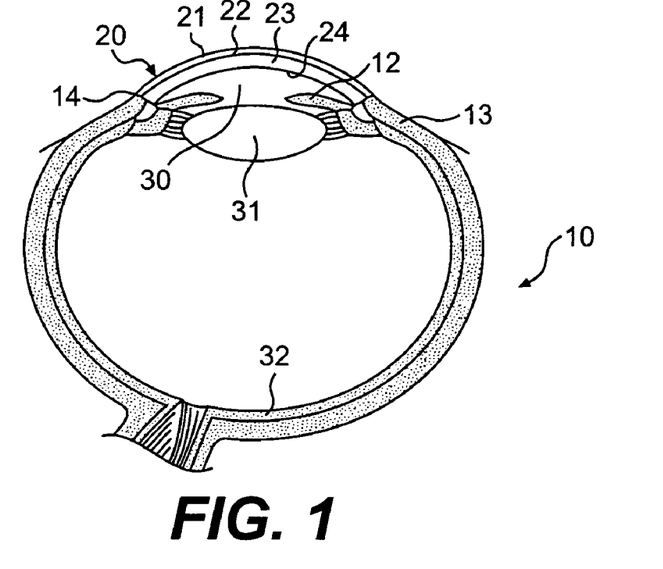
FIG. 1 is a side elevation, cross sectional view of an eye.
Figure 2:
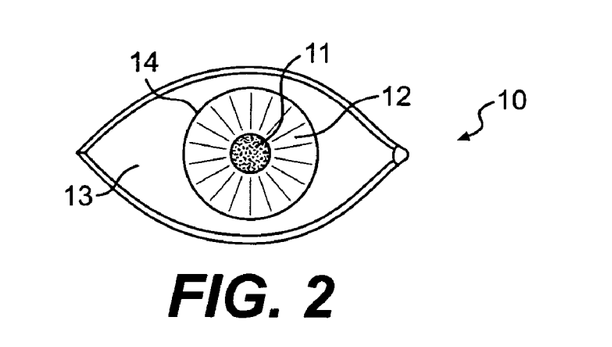
FIG. 2 is a front elevation view of an eye.

FIGS. 1 and 2 illustrate a human eye before its color has been modified in accordance with methods and inserts described herein. FIGS. 1 and 2 are used to define the parts of the eye as those terms are used herein. The eye 10 includes the round pupil 11 in the center of the eye. The pupil 11 is defined by the iris 12. The iris 12 may dilate or contract depending on the given lighting conditions that are present at a given time, so the pupil may be larger or smaller depending on conditions. The cornea 20 is the clear, layered portion of the eye 10 that allows light to pass into the eye. The cornea 20 has several layers. The epithelium 21 is the outer most layer of the cornea 20. Adjacent the epithelium 21 is the Bowman's membrane 22. The central portion of the cornea 20 is the stroma 23. The most inside, thin layer of the cornea 20 is the endothelium 24. The sclera 13 is the white portion of the eye surrounding the outside of the cornea 20. The boundary of the cornea 20 and the sclera 13 is the limbus 14. Behind the cornea 20 is the anterior chamber 30. The lens 31 is next. The retina 32 is the lining of the inside of the eye 10 that is able to differentiate and receive the light that is allowed in through the cornea 20 and lens 31.

Figure 3:
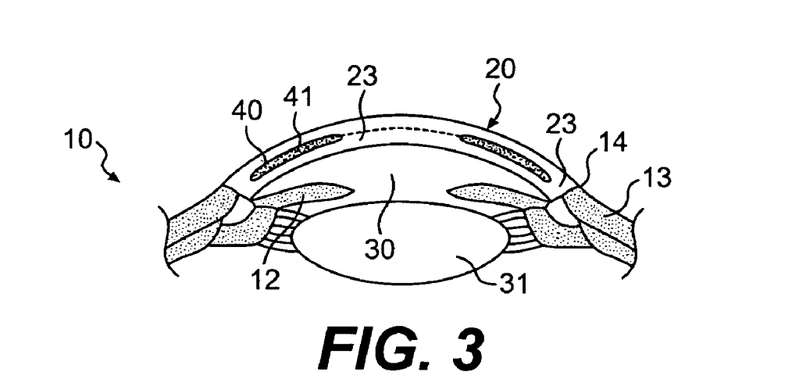
FIG. 3 is a side elevation, cross sectional view of the front portion of an eye.

FIG. 3 is a side view of the front portion of an eye 10 in which an insert 41 has been placed within a channel 40 in the stroma 23 of the eye. The channel 40 is a substantially flat, planar space that has been formed within the stroma 23. In this example, the channel 40 is annular in shape in that there is an outer diameter and an inner diameter that defines an opening within the inside of the inside diameter of the channel 40. As seen in FIG. 3, the width of the channel 40 is approximately the same width as the iris 12. In this way, the insert 41 that is placed within the channel 40 may adjust the apparent color of the iris 12 that is behind it. A second person who is looking at the eye 10 of the first person will view the color of the eye, as defined by the color of the iris 12 and insert 41, as a uniform color. As shown in FIG. 3 and FIGS. 3A-D, the outside diameter of the insert 41 is proximate the limbus 14, especially when viewed from the front of the eye 10. When the purpose of the channel 40 is solely as a space in which the insert 41 is placed, the channel is very thin. The channel 40 may have a thickness of approximately 1 micron. A laser technique can evaporate 1 micron or more of the stroma to create the channel. In one example, the thickness of the channel 40 is 3 microns or less with the material placed in it. The channel 40 can be created to make the net gain to the total thickness of the cornea 20 be approximately zero. The thickness of the channel 40 will depend on how thin of an insert 41 can still deliver color-modifying properties.

Figure 3A:
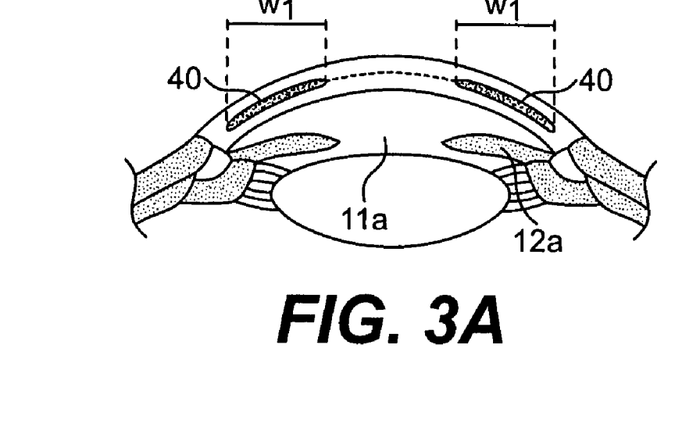
FIGS. 3A-D are similar to FIG. 3 but demonstrate variations in width of the channel described herein.
Figure 3B:
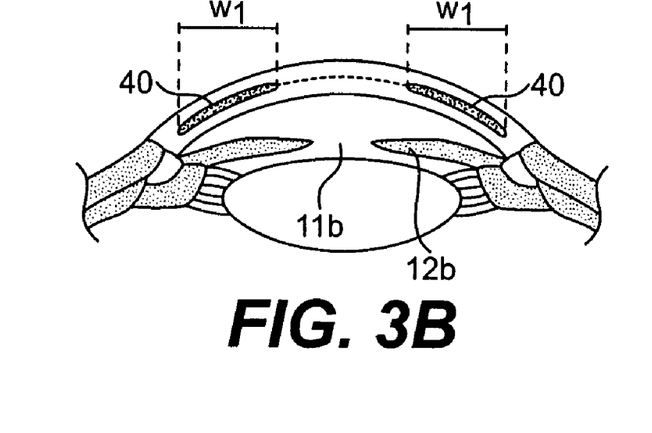
Figure 3C:
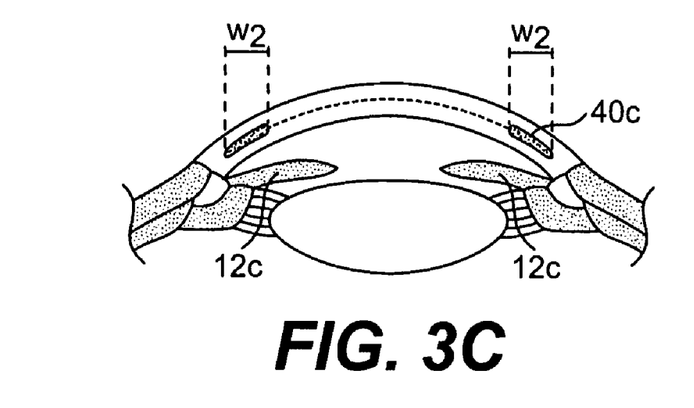
Figure 3D:
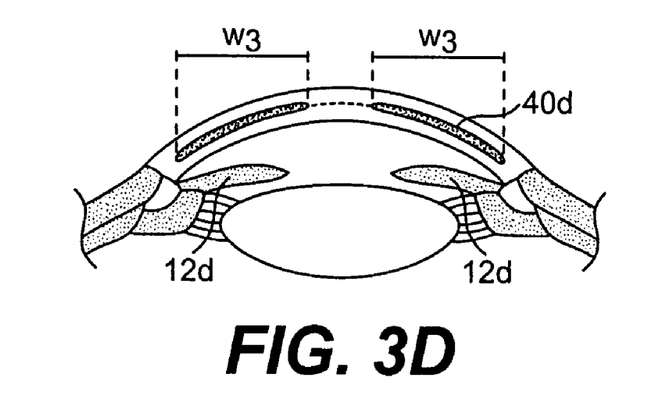

In FIGS. 3A and 3B, there is demonstrated the common anatomic situation where the width $W_1$ of the channel 40 remains constant, however the iris 12 may change from a particular size 12a, thereby creating a pupil size 11a to a more contracted size 12b, thereby creating a smaller pupil 11b. This would occur, for instance, when a person becomes subjected to relatively bright lighting conditions in FIG. 3B versus 3A. The width W of the channel 40 may be narrowed as shown in FIG. 3C where the width $W_2$ is substantially less than the width of the iris 12c. Alternatively, the width $W_3$ of the channel 40 may be wider than the iris 12d. Assuming that the iris 12 shown in FIG. 3 is of a size corresponding to normal daylight, then the inside diameter of the channel 20 is located so that it is proximate the normal daylight diameter of the iris. As is evident from the other alternatives shown, however, the width of the channel 40 may vary. For instance, in FIG. 3C, a patient may have congenital or traumatic damage to only the outside of the iris 12c. In that case, the channel 40c is only necessary to cover approximately the outside half of the iris in its normal daylight diameter. An insert may be relatively more colorized beyond the dilated pupil area to minimize night vision effects as necessary as determined by study.

As shown herein, the channel 40 substantially encircles the pupil 11 of the eye 10. In this way, a regular and consistent color or pattern of an insert 41 may give a regular eye pattern appearance. Also, the channel 40 is shown as generally being symmetrical. It does not need to be symmetrical. The inside diameter and outside diameter of the channel 40 may define a shape other than a circle. Also, the inside diameter may not be centered within the outside diameter of the channel 40. The shape of the channel 40 may be varied and adjusted as required by the specific circumstances of a given patient.

Figure 7A:
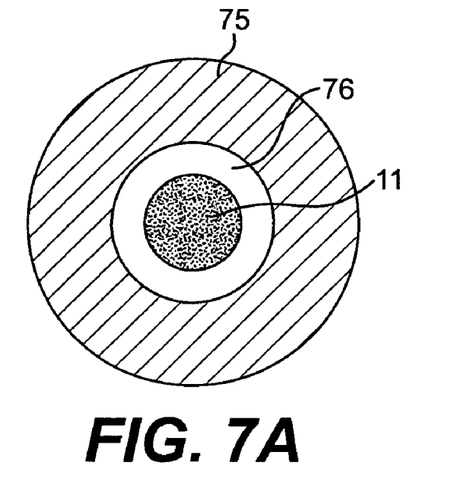
FIG. 7A is a view of the front of an eye having an insert around the pupil.

FIG. 7A shows an eye having an annular colored portion 75, the normal iris 76 inside the colored portion, and the pupil 71. This figure demonstrates that an insert that defines the colored portion 75 does not always cover and hide the iris 76. Anatomically, this is natural, as natural eye color often has different eye color shown across the width of an iris.

The insert 41 may be comprised of any material that includes portions that are opaque. An insert 41 is typically not completely opaque. Complete opacity inherently requires a solid object. For the health of the eye, the insert is required to be permeable to allow the flow of nutrients across the stroma 23. Examples of acceptable inserts 41 include a slurry of biocompatible material, a fabric including opacified material, and a thin permeable film material including some opaque materials. Of course others of skill in the art will devise other acceptable inserts that are covered by the scope of the present invention. Also, the insert 41 as shown has a relatively uniform color (degree of opacity) across the width. The insert 41 may alternatively have a color gradient or other variable pattern across its width. As noted earlier, it may be beneficial for night vision (when the pupil is relatively dilated) for the opacity at the center of the insert 41 (near the pupil 11) to be relatively low.

Figure 4:
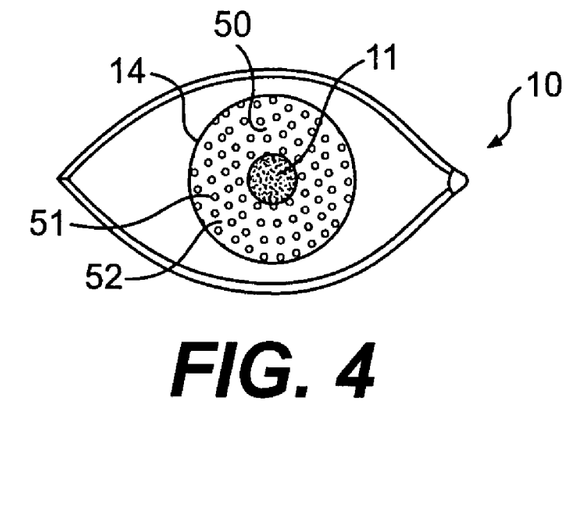
FIG. 4 is a front elevation view of an eye having a slurry of opacified material placed in a channel around the pupil.
Figure 4A:
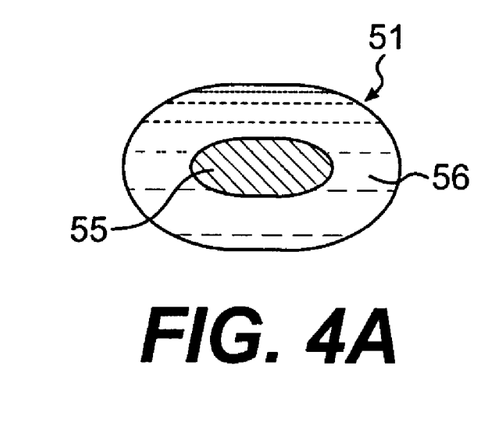
FIG. 4A is a side elevation, cross sectional view of a particle in the slurry shown in FIG. 4.

In FIG. 4, an eye 10 has an ordinary pupil 11 and an insert 50 surrounding the pupil. The insert 50 is above the iris that gives the visual effect of being the iris. The insert 50 is a slurry of biocompatible material that has been injected into the stromal channel 40 that has been formed directly above, the iris as described earlier herein in connection with, for example, FIGS. 3A-D. The biocompatible material is opacified in the color appropriate to accomplish the desired color change. For example, if deep blue eye color is the desired effect, a deep blue-gray, blue-purple or blue-blue slurry would be used. As shown in FIG. 4A, flat or spherical particles 51 are dispersed within a gel carrier 52 to form the slurry. The use of particles 51 permits fluid and nutrients to normally pass through the stromal tissue. The biocompatible material is placed in the channel in an appropriate density without altering the corneal shape, assuming that no shape change is desired. The particles 51 may be composed of many materials known to be biocompatible including hydrogels, polytetrafluoroethylene (PTFE), and polymethymethacrylate (PMMA). Referring to FIG. 4A, the particles 51 may include small beads 55 of PMMA that could be coated or otherwise dispersed inside of hydrogel 56 to further reduce any immune response to the foreign bodies in the stroma and to reduce movement and extrusion. The hydrogel 56 could also be dosed with anti-inflammatory agents to further reduce immune reactivity. The color used to tint the particle 51 could be stabilized in the hydrogel or in the PMMA or other slurry material to prevent leaching and potential toxicity. Even toxic materials can be encased in PMMA safely. The particles 51 should be small, under about 3 microns of thickness, to minimize refractive effect. The shape of the particles could be flat round, spherical, ovalized, diamond-shaped, star-shaped, triangular or any other geometric configuration that provides a desirable color effect or other visual effect with the least amount or predetermined amount of optical effect.

The biocompatible material may have UV absorbing quality and could reduce the UV exposure at the peripheral edge of the pupil 11. Likewise, in the event of a congenital or traumatic flaw in the pupil, the UV protecting material could prevent additional, unwanted light from getting into the inside of the eye. A clear insert could be fashioned over the pupil to provide UV protection and could also be oriented to provide polarizing effect and/or could be photograying or otherwise photoreactive The peripheral part of the insert could be colored and may contain two- or three-dimensional patterns.

It is expected that the particles will include current materials used in contact lens and other optical applications. Ideally, the biocompatible material will display even color distribution, will have minimal to no refractive or refractile quality, will be stable and non-inflammatory, and will remain stable in place in the stroma without drifting or extrusion. Although, as noted earlier, the material may be more or less tinted across the width of the channel for various, intended purposes.

Figure 10:
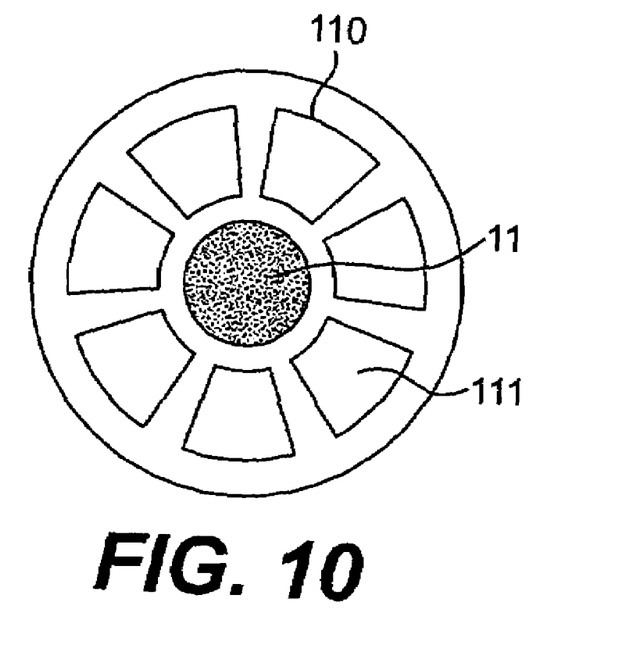
FIG. 10 is a view of the front of an eye having a plurality of channels with inserts therein.

Currently, color is provided by contact lens through use of linear sections of color in various patterns that are designed to fool an observer into seeing the color as one does with the iris of the eye. Referring to FIG. 10, linear inlays could be fashioned using a slurry of materials and placed in the stromal space in a manner to duplicate this effect. As shown in FIG. 10, radial channels 110 extend from an inside end proximate the pupil 11 outwardly. An insert 111 is placed within each channel 110. The insert 111 may be the slurry already discussed herein or the fabric or film discussed subsequently herein. The radial channels 110 may be formed all around the pupil 11 or only partially around it. The width and number of radial channels 110 may also vary as needed. The fabric or film insert that may be placed in a radial channel 110 may be rolled and inserted by using a plunger and syringe that is injected into each channel.

Figure 5:
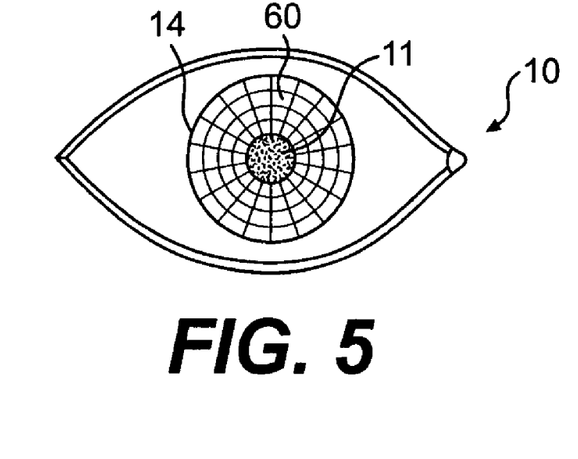
FIG. 5 is a front elevation view of an eye having a fabric insert in a channel around the pupil.

Another type of acceptable biocompatible material that may be placed within the channel 40 is a fabric 60 of at least partially opacified material as shown in FIG. 5. The fabric insert 60 may be woven, spun, non-woven, electrospun, or any other type of fibrous substrate. Inherently, the fabric that is placed into the channel has gaps and holes to allow for healthy permeability through the fabric. The fabric may itself be the web that opacifying material is supported by, or the fabric could be comprised of fibers that are impregnated with the opacifying material. The use of a fabric insert 60 allows the introduction of a uniform amount of material into a channel within the stroma. The fabric may also facilitate removal of the insert if this ever became necessary or desirable. The fabric may be comprised of any biocompatible materials including, but not limited to, natural polymers (e.g., collagen and fiberin), synthetic polymers, PMMA, hydrogel, PTFE, stabilized hydrophilic polymers and newer biologically stabilized materials. These materials, along with the inherent porous nature of the fabric, allow for the transfer of nutrients and oxygen across the insert. The fabric insert may have any thickness that does not materially affect the refractive performance of the eye when placed for color modification only. Thicknesses included, in some examples, 5 microns or less or 3 microns or less. It can also be seen that the fabric may include patterns that are woven or otherwise formed within the fabric. The patterns may include a gradient of opacity from least opaque in the center to more opaque when moving outwardly.

Figure 6:
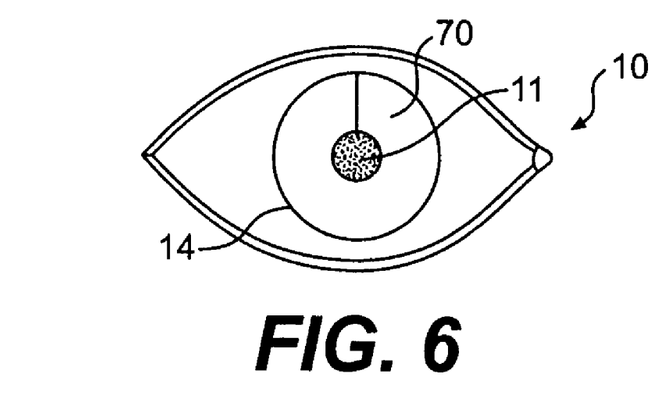
FIG. 6 is a front elevation view of a thin film insert in a channel around the pupil.

A still further alternative insert includes a thin polymer film that is nevertheless highly permeable. It must be very thin to allow for color without refractive change. Preferably, the solid film insert 70 has a thickness of 5 microns or less or, alternatively, 3 microns or less. The solid film insert 70 is placed outside the pupil margin and could be extruded into place within the channel using an injection system similar to those systems used in refractive implant surgery currently. Acceptable film materials include those referenced earlier with respect to the fabric of opacified material. Those of skill in the art will understand how to treat or process the film in order to obtain sufficient permeability to provide for nutrients flow through the insert 70. Films may be also imprinted with various patterns and color gradients. If the film was thin it could pass over the pupil and this area could contain additives having UV and/or polarizing effects without affecting vision. The thinner the material, the better the permeabilty and the more likely that the eye will tolerate the material long term.

Figure 7B:
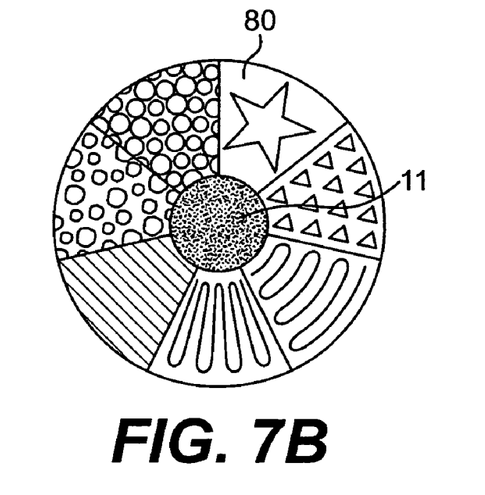
FIG. 7B is a view of the front of an eye having different possible designs implantable in the stroma.

As indicated earlier, the visual appearance of the insert may be carefully prepared to mimic a human iris. Alternatively, other natural or geometric designs may be desired for therapeutic or cosmetic purposes. FIG. 7B is a visual example of different designs that may be displayed in an insert 80. Most likely, the seven different designs shown in the insert 80 and other designs would not be used together. However, it is possible that a person would want more than one geometric design to be visible in the eye. Further, it may be therapeutically important to have different visual effects across the area of the insert 80. For instance, the amount of UV absorbance may be graded across the width of the insert.

While all of the figures display an insert that maintains an inside opening corresponding to the pupil 11, there is no requirement that the insert could not likewise span across the pupil 11. This is something that must be done carefully in view of the potential distortion of the visual light that maybe received by the human eye. However, for instance in the example of a very sensitive retina, a person might therapeutically benefit from UV protection across the entire cornea.

The insert and channel and discussion herein has emphasized the minimal or lack of effect of the insert on the refractive performance of the eye. However, it is possible to use these inserts and the process of placing them in the eye to alter corneal curvature and to match the eye to wavefront topography or other aberrational systems and to shape the cornea to a more perfect oblate shape. To this end, the insert could be made thicker or thinner in the area needed to match the shape or wavefront topography. The insert could be made slightly thicker or thinner to give the effect of normalizing the corneal curvature. Many aberrational visual effects occur at the periphery of the vision, and these could be positively altered by the use of a custom-shaped peripheral insert as described herein. Inserts that alter this curvature to flatten the periphery offer the potential of reducing these aberrational effects and improving vision. Since the inserts depicted here are placed in the peripheral part of the eye they could be placed with thickness to reverse the curvature change and reduce the variety of aberrations that are related to corneal curvature. The ability of the material to absorb a certain wavelength of light and to be altered in shape could be an excellent adjunct to current techniques of treating the corneal stroma. In one alternative, the insert may be preformed externally and placed within the cornea. The opacified material may be especially selected for the purpose of fine tuning the shape of the insert at a later date, because the material may absorb light energy and specific wave lengths that would allow the material to expand or contract upon heating. This allows for matching refraction or aberration with an external treatment.

Still further additionally, the biocompatible material that makes up the insert may further include photochromatic components. These components may darken or lighten as a result of the effective light or other energy such as magnetism. This type of material could be used to externally manipulate the eye color or improve solar protection.

Different methods may be used to modify eye color. In the broadest terms, the different methods include use of a surgical blade and/or a type of laser. A common procedure currently includes use of a microkerotome to cut through the outer cornea creating a corneal "flap" that is lifted up to expose the stroma. For the purpose of the present method, the microkerotome or other surgical blade could be used to create the channel into which a colored insert may be placed. Microkeratomes were designed to create a "window" called a flap under which a 5 to 10 millimeter laser treatment would be placed. Therefore the current design of microkerotomes is probably too small for this purpose. Different modified keratomes could be developed. Ideally the flap does not need to be created and a channel could be made by another method.

An alternative, a laser-based method includes the use of a pulsion femtosecond laser. This laser eliminates the need for a microkerotome cut by instead generating a rapid, low-energy plasma pulse to separate the cornea from the stroma. After the stroma is separated from the stroma, a small slit may be cut in the cornea to gain access to the channel formed by the laser. The slit is preferably made in the cornea above the upper eyelid or below the lower eyelid. This slit is then used to place the insert into the channel. In the example of a slurry, the material may be injected around the channel. The fabric or film may have a cut across it to create an end that may then be taken around the channel. Further, the fabric or film could be extruded into the channel with an inserter that pushes out the insert as the surgeon withdraws the inserter out of the channel.

Figure 11:
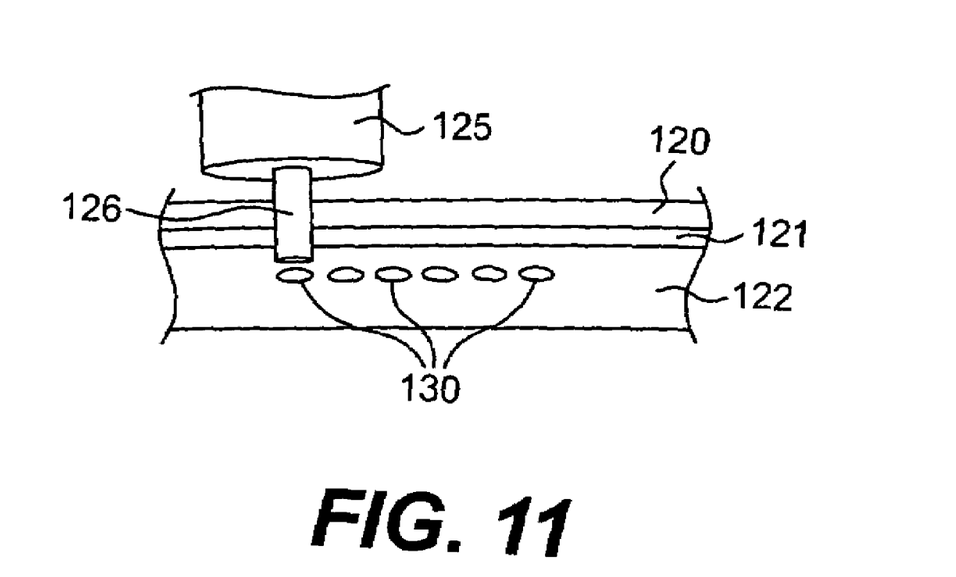
FIG. 11 is a side elevation, cross-sectional view of an eye having opacified material injected into it.

A tattoo technique may also be used to place the particles into the stroma or Bowman's membrane layering the particles under the surface and in the stroma at the same or similar level as the channel and being extruded into the channel area with a needle. As shown in FIG. 11, a syringe 125 having a needle 126 of predetermined length is used to inject particles 130 or a slurry into the stroma 132 at a specific depth. The needle 126 passes through the epithelium 120 and Bowman's membrane 121. Like a tattoo, many different designs are possible.

The depth of the channels would in general be in the stroma and under the Bowman's membrane and would be developed by experience. In one example, the depth would be at the 100 to 150 micron level. An alternative argument would be to place inserts deeper into the stroma to allow for corrective procedures on the surface of the eye. The width would be from the mesoptic pupil edge to the limbus or near the limbus. An alternate approach would be to have the channels be radial tracks moving toward the pupil from the limbus. These would be, in one example, 1 to 2 millimeters wide and at the same depth. The inserts could be inserted with an extrusion instrument and could be withdrawn down the same path if necessary. These tracks would be created with the femtosecond laser or with a bladed instrument similar to the intrastromal implants known as Intacs. They also could be graded in thickness to allow for refractive alteration as well.

Figure 8:
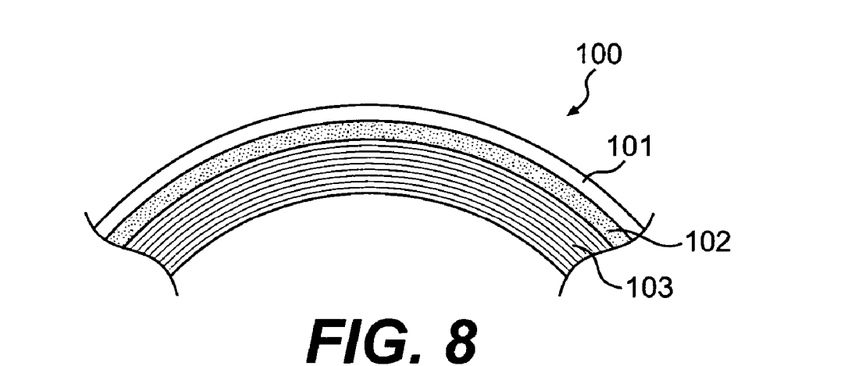
FIG. 8 is a side elevation cross sectional view of the cornea of an eye.
Figure 9:
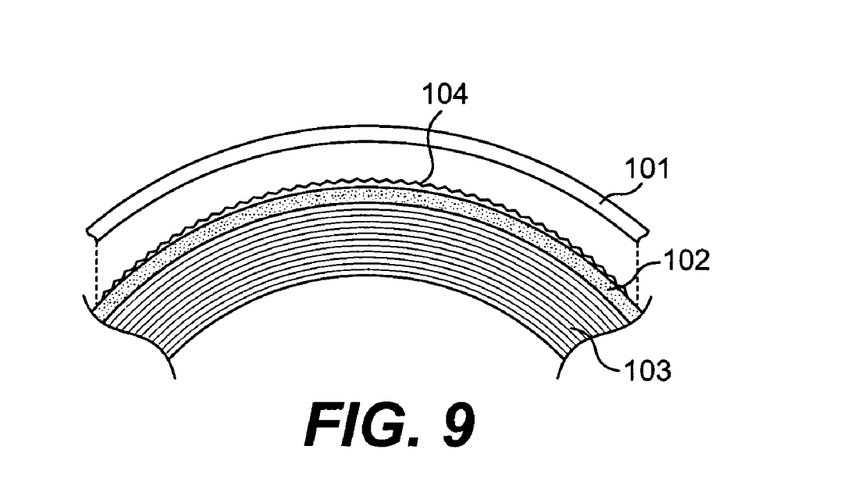
FIG. 9 is a side elevation view of the cornea shown in FIG. 8 wherein the Bowman's membrane has been stained with a pigment.

A still further method of modifying eye color is demonstrated in FIGS. 8 and 9. In this alternative method, the epithelium 101 of a cornea 100 is removed from the top of the eye. This exposes the Bowman's membrane 102. The portion of epithelium 101 that is removed is preferably annular in shape to leave intact the entire cornea along the optic axis of the eye. The Bowman's membrane 102 may then be stained or tattooed with a dye 104 to an appropriate color or design or other visual image. Then the epithelium 101 either grows back or is placed back on top of the Bowman's membrane 102, thereby encapsulating the dye and resulting in modified eye color. In this example, the epithelium 101 may be separated from the Bowman's membrane 102 using laser techniques, or alternatively using surgical blade-based techniques (e.g., using an epikeratome).

While the invention has been described with reference to specific embodiments thereof, it will be understood that numerous variations, modifications and additional embodiments are possible, and all such variations, modifications, and embodiments are to be regarded as being within the spirit and scope of the invention.

What is claimed is:

1. A method of modifying eye color comprising the steps of:
    forming an annular channel within a plane around and encircling the pupil of an eye, wherein the channel is located in the stroma portion of the eye and has annular borders proximate the limbus and the daylight margin of the pupil,
    slitting the cornea of the eye to gain access to the channel,
    inserting into the channel a biocompatible material, wherein the biocompatible material comprises a slurry of particles having a thickness of approximately 1-3 microns, and being at least partially opacified in a color appropriate to accomplish a desired color change wherein the shape of the particles comprise a shape selected from the group consisting of flat round, spherical, ovalized, diamond shaped, star shaped, triangular, and combinations thereof; and
    wherein the net gain to the total thickness of the cornea is approximately zero, and the inserted material does not materially affect the refractive performance of the cornea while providing said color change and said material permits fluid and nutrients to pass through the stromal tissue.

2. A method of modifying eye color as described in claim 1, wherein the channel is formed by using a laser technique.

3. A method of modifying eye color as described in claim 2, wherein the laser technique includes the use of a femtosecond laser.

4. A method of modifying eye color as described in claim 1, wherein the channel is formed by using a surgical blade.

5. A method of modifying eye color as described in claim 4, wherein the surgical blade is a microkeratome.

6. A method of modifying eye color as described in claim 1, wherein the channel extends around the entire circumference of the pupil.

7. A method of modifying eye color as described in claim 1, wherein the slitting step comprises forming a slit in the cornea near the limbus and above the margin of the upper eye lid or below the margin of the lower eye lid.

8. A method of modifying eye color as described in claim 1, wherein the biocompatible material is comprised of the slurry of particles with at least some of the particles comprising an opacified material.

9. A method of modifying eye color as described in claim 8, wherein the slurry of particles comprises a hydrogel.

10. A method of modifying eye color as described in claim 8, wherein the slurry of particles comprises polymethylmethacrylate.

* * * * *